United States Patent [19]
Jeffers et al.

[11] Patent Number: 5,258,002
[45] Date of Patent: Nov. 2, 1993

[54] DUAL TAPERED SURGICAL KNIFE

[75] Inventors: Mark J. Jeffers, Fort Worth, Tex.; Michael S. O'Neil, Shillington; Luther A. Hoffman, Sinking Springs, both of Pa.

[73] Assignee: Alcon Surgical, Inc., Fort Worth, Tex.

[21] Appl. No.: 982,260

[22] Filed: Nov. 25, 1992

Related U.S. Application Data

[63] Continuation of Ser. No. 878,251, May 4, 1992, abandoned.

[51] Int. Cl.⁵ ............................................. A61B 17/32
[52] U.S. Cl. ..................................................... 606/167
[58] Field of Search ................ 606/166, 167; 30/346, 30/347, 348, 355, 356

[56] References Cited

U.S. PATENT DOCUMENTS

| | | |
|---|---|---|
| 3,367,335 | 2/1968 | Ward et al. |
| 3,798,688 | 3/1974 | Wasson ................................ 30/355 |
| 4,688,570 | 8/1987 | Kramer et al. ...................... 606/166 |

OTHER PUBLICATIONS

Eagle Laboratories ophthalmic surgical knife catalog.
AMO® ophthalmic surgical knife catalog entitled *Start With a Great Opening. AMO® MicroSurgical Blade System* (1991) Allergan, Inc.
Prime Surgical, Incorporated ophthalmic surgical knife catalog entitled *The Precise Blades for Precision Surgery, Micro and Special Surgery Incision Systems, Ear, Cataract, Keratome, Microsurgical, Lamellar, Slit, Needle, Scleral, Myringotomy, Round, Plastic, MVR and Miniature Edged.*
Beaver® ophthalmic surgical knife catalog entitled *The Standard for Quality, Responsiveness and Innovation in Blades and Instruments for the Ophthalmic Surgeon.* (1990) Becton Dickinson and Company.

*Primary Examiner*—Stephen C. Pellegrino
*Assistant Examiner*—William Lewis
*Attorney, Agent, or Firm*—Jeffrey S. Schira

[57] ABSTRACT

A surgical knife having a handle and a blade, the blade having a blunt tip, a generally V-shaped cutting portion extending from the blunt tip to the widest part of the blade and tapered portion extending from the widest part of the blade to the point of attachment of the blade with the handle.

15 Claims, 2 Drawing Sheets

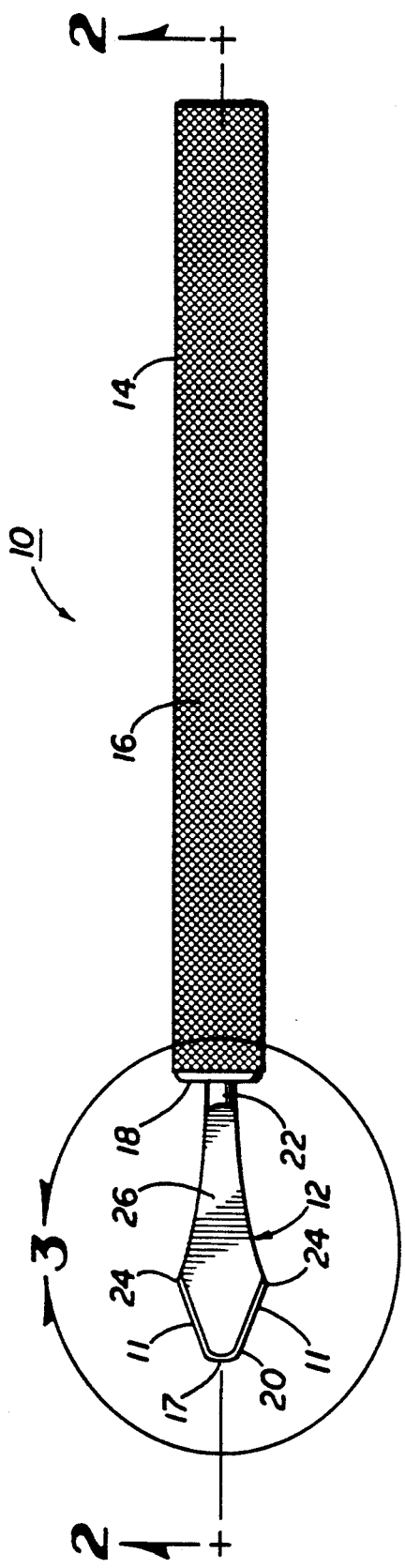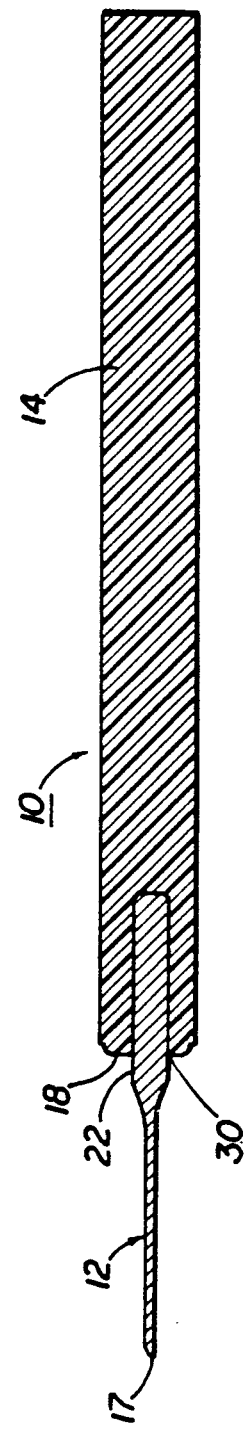

DUAL TAPERED SURGICAL KNIFE

This application is a continuation of application Ser. No. 07/878,251, filed May. 4, 1992, abandoned.

BACKGROUND OF THE INVENTION

The present invention relates to surgical knives and particularly to knives used in ophthalmic surgery.

For many years, the predominant method of treating a diseased lens has been to remove the diseased lens and replace it with an intraocular lens ("IOL"). Two surgical procedures are preferred for removing the diseased lens: extracapsular cataract extraction and phacoemulsification. Extracapsular cataract extraction involves removing the lens in a relatively intact condition by use of a vectus or similar surgical instrument. Phacoemulsification involves contacting the lens with the vibrating cutting tip of an ultrasonically driven surgical handpiece to emulsify the lens, thereby allowing the emulsified lens to be aspirated from the eye. Although extracapsular cataract extraction has been the preferred surgical technique, phacoemulsification has become increasingly popular, in part because the cutting tip of the ultrasonic handpiece requires only a relatively small (approximately 3 to 3.5 millimeter) tunnel incision.

A typical posterior chamber IOL comprises an artificial lens ("optic") and at least one support member ("haptic") for positioning the IOL within the capsular bag. The optic may be formed from any of a number of different materials, including polymethylmethacrylate (PMMA), polycarbonate and acrylics, and it may be hard, relatively flexible or even fully deformable so that the IOL can be rolled or folded prior to insertion. The haptics generally are made from some resilient material, such as polypropylene or PMMA. IOL's may be characterized as either "one-piece" or "multi-piece." With one-piece IOL'S, the haptic and the optic are formed integrally as a blank and the IOL is then milled or lathed to the desired shape and configuration. Multi-piece IOL's are formed either by attaching the haptic to a preformed optic or by molding the optic around the proximal end of the haptic.

The diameter of the optic varies depending on the design of the IOL, but an optic diameter of around 5-6 millimeters (mm) is most common. Although some IOL's are made from a foldable material, allowing the IOL to be inserted through the typical 3 mm to 3.5 mm incision used with phacoemulsification, in general, the incision must be enlarged after the aspiration of the cataractous lens to allow the IOL to be implanted. Surgeons typically use a surgical knife with a blade width of approximately 3.2 mm for making the initial incision into the-anterior chamber and for widening the incision to approximately 5.2 mm for IOL insertion. While the knife must have a sharp point to make the initial incision, the sharp point is not needed to widen the incision, as an elongated or sharp point increases the possibility of damage to the iris or capsular bag. Therefore, the knife used to widen the initial incision preferably has a short, blunt nose.

Two prior art surgical knives sold for use as IOL implant knives have generally chevron-shaped blades, with blunt, V-shaped noses and parallel cutting sides. While the blunt noses reduce the risk of injury to the iris or capsular bag, the parallel sides increase the likelihood that the incision will be unnecessarily widened, particularly if there is any unintentional side-to-side movement of the knife while it is within the incision.

Accordingly, a need continues to exist for a surgical knife that will precisely cut the IOL implant incision used in phacoemulsification while at the same time, minimizing the likelihood of iris or capsular bag injury and unintentional widening of the incision.

BRIEF SUMMARY OF THE INVENTION

The present invention improves upon prior art surgical knives by providing a knife with a dual tapered blade. The blade contains a rounded, blunt tip that flares or tapers so that, at its widest point, it is approximately 5.30 mm wide, the incision width preferred by many surgeons for IOL implantation. This maximum width occurs at only one point along the length of the blade, and the blade narrows or tapers to its point of attachment with the handle. The rounded, blunt tip and dual tapered design of the surgical knife of the present invention minimizes the risk of injury to the iris or capsular bag while at the same time, reduces the likelihood of unintentional widening of the incision.

Accordingly, one objective of the present invention is to provide a surgical knife capable of making the IOL implant incision used for phacoemulsification.

Another objective of the present invention is to provide a surgical knife that has a blunt, rounded tip.

Another objective of the present invention is to provide a surgical knife that has a blade that flares or tapers from its tip to a point of maximum width and then narrows to the blade's point of attachment with the handle.

Another objective of the present invention is to provide a surgical knife that minimizes the risk of injury to the iris or capsular bag.

These and other objectives and advantages of the present invention will become apparent from the detailed description, drawings and claims that follow.

BRIEF DESCRIPTION OF THE DRAWING

FIG. 1 is a plan view of the surgical knife of the present invention.

FIG. 2 is a cross-sectional view of the knife illustrated in FIG. 1 taken along line 2—2.

DETAILED DESCRIPTION OF THE INVENTION

Figure 3:
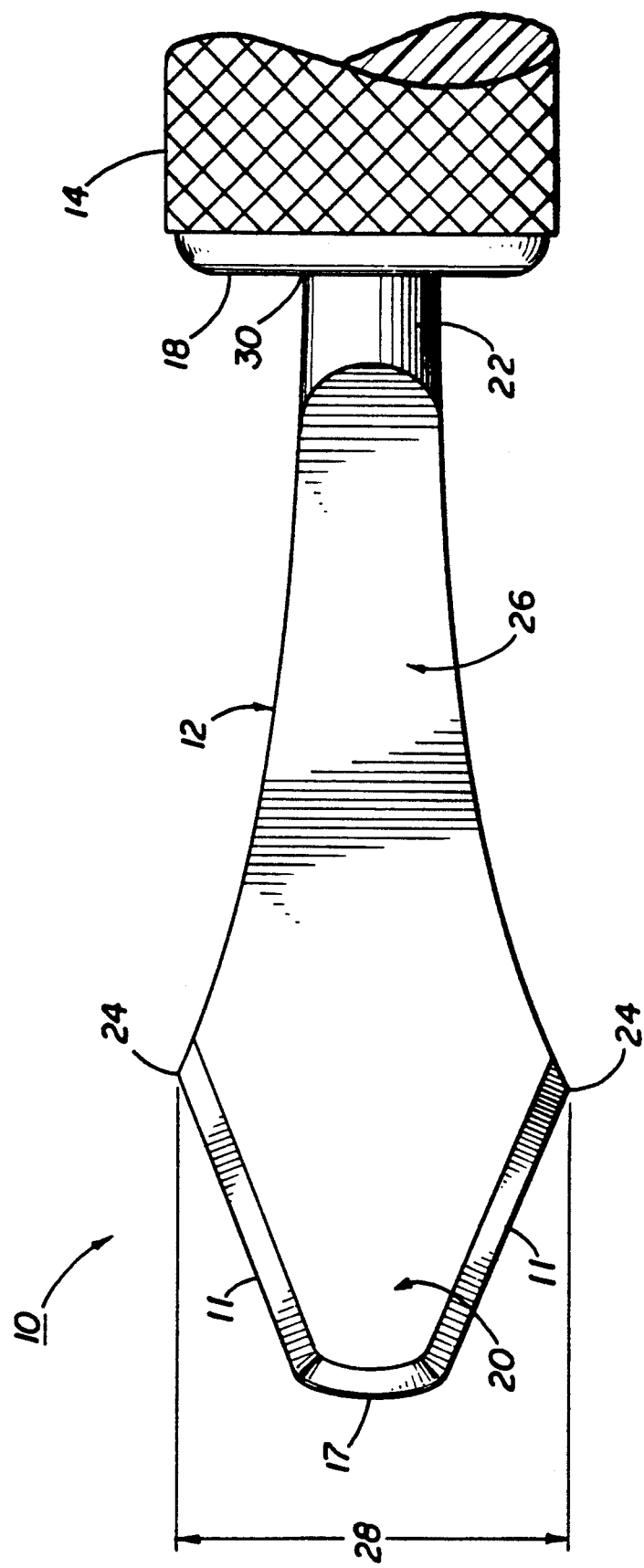
FIG. 3 is an enlarged plan view of the surgical knife of the present invention taken at circle 3 on FIG. 1.

As can be seen in FIGS. 1, 2 and 3, surgical knife 10 of the present invention includes a blade 12 and a handle 14. Knife 10 may be either reusable or disposable. If knife 10 is reusable, blade 12 may be made of any suitable material such as stainless steel or titanium and handle 14 may be made from stainless steel, titanium, or aluminum. If knife 10 is disposable, handle 14 also may be made of suitable thermoplastic, fiberglass or composite material. Handle 14 is preferably cylindrical, although other cross-sectional shapes may also be used, and may contain knurling or other suitable roughening 16 to make handle 14 more positive to grip.

As can be seen in FIG. 2, blade 12 preferably has a thin cross-section (approximately b 0.5 mm) and may be formed either from a sheet material or (as shown in FIGS. 1, 2 and 3) by flattening the end of round wire 22 with an approximate diameter of 1.5 mm. Blade 12 may be straight, as shown in FIG. 2, or angled relative to handle 14. Blade 12 also contains blunt, rounded tip 17 and sharpened side edges 11 and is attached to end 18 of handle 14 by any conventional means such as integrally molding blade 12 within handle 14 or a collet (not shown). Tip 17 is preferably between 1.5 mm and 2.5 mm wide so as to fit easily through the typical incision used for the phacoemulsification cutting tip. As can best be seen in FIG. 3, cutting end 20 of blade 12 opposite handle end 18 is generally V-shaped from tip 17 to medial portion 24 so that maximum width 28 of blade 12 at medial portion 24 is approximately between 5.1 and 5.4 mm, with 5.30 mm being preferred. Cutting edges 11 are preferable ground at an angle of approximately between 25° and 55° relative to the plane in which blade 12 lays. The length of cutting end 20 between tip 17 and medial portion 24 is approximately between 3.5 and 4.5 mm, with 4.0 mm being preferred. Tapered portion 26 of blade 12 extends between medial portion 24 and attachment point 30 of blade 12 on handle 14. Tapered portion 26 of blade 12 narrows or tapers so that the width of blade 12 at handle 14 is no larger that the diameter of wire 22 used to form blade 12 (approximately 1.5 mm).

In use, once phacoemulsification is complete, the surgeon fully inserts cutting end 20 of blade 12 into the incision, widening the incision to maximum width 28 of blade 12 at medial portion 24, the widest part of blade 12, and removes knife 10. Unintentional rocking or yawing of blade 12 within the incision is less likely to cause the incision to be widened beyond maximum width 28 of blade 12 because maximum width 28 occurs only at medial portion 24. Further, blunt, rounded tip 17 reduces the likelihood that tip 17 will contact or injury the iris or capsular bag.

This description is given for purposes of illustration and explanation. It will be obvious to those skilled in the relevant art that modifications may be made to the invention as described herein without departing from its scope or spirit.

We claim:
1. A surgical knife, comprising:
   a. a handle; and
   b. a blade attached to the handle having
      i) a dull, blunt tip,
      ii) a generally V-shaped cutting end with a pair of cutting edges,
      iii) a maximum width and
      iv) a dull tapered portion extending from the maximum width to a point of attachment with the handle.
2. The surgical knife of claim 1 wherein the maximum width is approximately between 5.1 millimeters and 5.4 millimeters.
3. The surgical knife of claim 2 wherein the maximum width is approximately 5.30 millimeters.
4. The surgical knife of claim 1 wherein the blade comprises stainless steel.
5. The surgical knife of claim 1 wherein the blade comprises titanium.
6. The surgical knife of claim 1 wherein the handle comprises stainless steel.
7. The surgical knife of claim 1 wherein the handle comprises thermoplastic.
8. The surgical knife of claim 1 wherein the handle comprises aluminum.
9. A surgical knife, comprising:
   a. a handle; and
   b. a blade attached to the handle having
      i) a dull, blunt tip,
      ii) a generally V-shaped cutting portion with a pair of cutting edges.
      iii) a medial portion having a maximum width of approximately between 5.1 millimeters and 5.4 millimeters and
      iv) a dull tapered portion extending from the medial portion to a point of attachment with the handle.
10. The surgical knife of claim 9 wherein the maximum width is approximately 5.30 millimeters.
11. The surgical knife of claim 9 wherein the blade comprises stainless steel.
12. The surgical knife of claim 9 wherein the blade comprises titanium.
13. The surgical knife of claim 9 wherein the handle comprises stainless steel.
14. The surgical knife of claim 9 wherein the handle comprises thermoplastic.
15. The surgical knife of claim 9 wherein the handle comprises aluminum.

* * * * *